United States Patent [19]

Gentelia et al.

[11] Patent Number: 5,201,714
[45] Date of Patent: Apr. 13, 1993

[54] LAPAROSCOPIC CANNULA

[75] Inventors: John S. Gentelia, Madison; Frank Williams, Frankfort; William Wheatley, Utica; Sharyn Longo, Frankfort; Deborah Forbey, Smyrna, all of N.Y.

[73] Assignee: Conmed Corporation, Utica, N.Y.

[21] Appl. No.: 846,386

[22] Filed: Mar. 5, 1992

[51] Int. Cl.⁵ ............... A61M 5/178; F16L 37/28; A61B 17/34
[52] U.S. Cl. .................. 604/167; 604/250; 251/149.2; 606/185
[58] Field of Search ............ 604/117, 164–170, 604/246, 247, 250, 256, 264; 606/184, 185; 128/754; 251/9, 149.2, 149.6

[56] References Cited

U.S. PATENT DOCUMENTS

| 299,532 | 6/1884 | Fitch | 604/250 X |
|---|---|---|---|
| 2,858,095 | 10/1958 | Harris et al. | 251/9 |
| 3,194,452 | 7/1965 | Sandeford | 251/9 X |
| 3,994,287 | 11/1976 | Turp et al. | |
| 4,177,814 | 12/1979 | Knepshield et al. | |
| 4,261,357 | 4/1981 | Kontos | 604/169 |
| 4,535,773 | 8/1985 | Yoon | 604/51 |
| 4,586,694 | 5/1986 | Jones | 251/149.2 |
| 4,634,421 | 1/1987 | Hegemann | 604/34 |
| 4,654,030 | 3/1987 | Moll et al. | |
| 4,655,752 | 4/1987 | Honkanen et al. | |
| 4,842,591 | 6/1989 | Luther | |
| 4,857,062 | 8/1989 | Russell | |
| 4,917,668 | 4/1990 | Haindl | |
| 4,931,042 | 6/1990 | Holmes et al. | |
| 5,041,097 | 8/1991 | Johnson | 604/167 |
| 5,066,288 | 11/1991 | Deniega et al. | |
| 5,108,380 | 4/1992 | Herlitze et al. | 604/283 |
| 5,127,626 | 7/1992 | Hilal et al. | 251/149.1 |

FOREIGN PATENT DOCUMENTS 2845643 4/1980 Fed. Rep. of Germany ...... 604/169

Primary Examiner—John D. Yasko
Assistant Examiner—Adam J. Cermak
Attorney, Agent, or Firm—Larson & Taylor

[57] ABSTRACT

A cannula is provided for laparoscopic surgery wherein the cannula comprises a housing and elongated tube with a passageway formed within the housing so that laparoscopic instruments may be passed through the housing and the elongated hollow tube into the abdominal cavity of a patient. A pair of rollers are mounted within the housing, the rollers being spring-urged together to close the passageway through the housing when an instrument is withdrawn. A slidable plate having apertures of different sizes are mounted in the housing with the apertures provided with slitted seals therein to close the passageway through the housing. The varying sized apertures in the slidable plate permit laparoscopic instruments of varying diameters to be used and to maintain an effective seal around the instrument. In another embodiment of the cannula a valve is provided which is closed when the rollers within the housing are in engagement with each other. When a laparoscopic instrument is passed through the housing to separate the rollers, the valve moves to an opened position to permit the laparoscopic instrument to pass therethrough.

8 Claims, 3 Drawing Sheets

LAPAROSCOPIC CANNULA

BACKGROUND OF THE INVENTION

The field of the invention relates to medical instruments and more specifically to a cannula for use with laparoscopic instruments to permit the passage of laparoscopic instruments through the cannula while maintaining a seal around the instruments.

The use of cannulas in laparoscopic surgery is well known. In laparoscopic surgery an incision is made by means of a trocar and the abdomen is filled with carbon dioxide gas. The cannula which maintains the incision open to receive surgical instruments must be kept closed to prevent the escape of the gas. Many prior art cannulas utilize a trapdoor within the housing of the cannula with the trapdoor being spring pressed to a closed position The trapdoor opens when an instrument is passed through the cannula. However, quite frequently the laparoscopic instrument has a curved tip or other structure which will catch on the trapdoor and thus prevents the removal of the instrument from the cannula. Cannulas of this type are shown in the Moll et al U.S. Pat. No. 4,654,030 and the Deniega et al U.S. Pat. No. 5,066,288.

Prior art cannulas are designed with flexible seals to permit passage of instruments through the cannula without permitting gas within the abdominal cavity from leaking through the cannula. However, such seals are generally designed for a single size of instrument and when instruments of varying diameters are used, the seals are ineffective and permit the escape of gas from the abdominal cavity. The present invention overcomes the above-noted disadvantages of prior art cannulas.

SUMMARY OF THE INVENTION

The present invention overcomes the disadvantages of prior art cannulas by providing a cannula having a pair of spring pressed rollers which are urged to a position wherein the rollers block off the passageway within the cannula to prevent gas within the abdominal cavity from escaping to atmosphere. A slidable plate is mounted on the housing with the slidable plate having a series of variable sized openings therein with each of the openings having slitted flexible seals therein. Thus, laparoscopic instruments of different sizes are matched with the aperture sizes in the slotted plate and the selected sealed aperture is positioned in alignment with the passageway through the cannula. Thus, effective sealing of the passageway can be achieved even when various sized instruments are used.

In another embodiment of the present invention, a flexible valve is positioned within the housing immediately beneath the rollers. A pair of arms are mounted on the rollers with the arms adapted to close the flexible valve when the rollers are in engagement with each other. When the rollers are separated by forcing a laparoscopic instrument between the rollers, the arms which engage the flexible valve move apart sufficiently to permit the laparoscopic instrument to pass through the cannula.

An object of the present invention is to provide a cannula for use in laparoscopic surgery which provides for effective sealing of the passageway in the cannula for instruments of varying sizes.

Another object of the present invention is to provide a cannula having a slidable plate with various sized apertures therein and sealing means within the apertures so as to provide effective sealing of the cannula with various sized laparoscopic instruments.

Another object of the present invention is to provide a flexible valve within a cannula and a pair of arms which are spring pressed to maintain the flexible valve in a closed position with the arms opening in response to passage of a laparoscopic instrument through the cannula to permit the flexible valve to open sufficiently to permit the instrument to pass therethrough.

Other objects and many of the attendant advantages of the present invention will become more readily apparent upon consideration of the detailed specification in connection with the accompanying drawings wherein:

DETAILED DESCRIPTION OF THE PREFERRED EMBODIMENT

Figure 1:
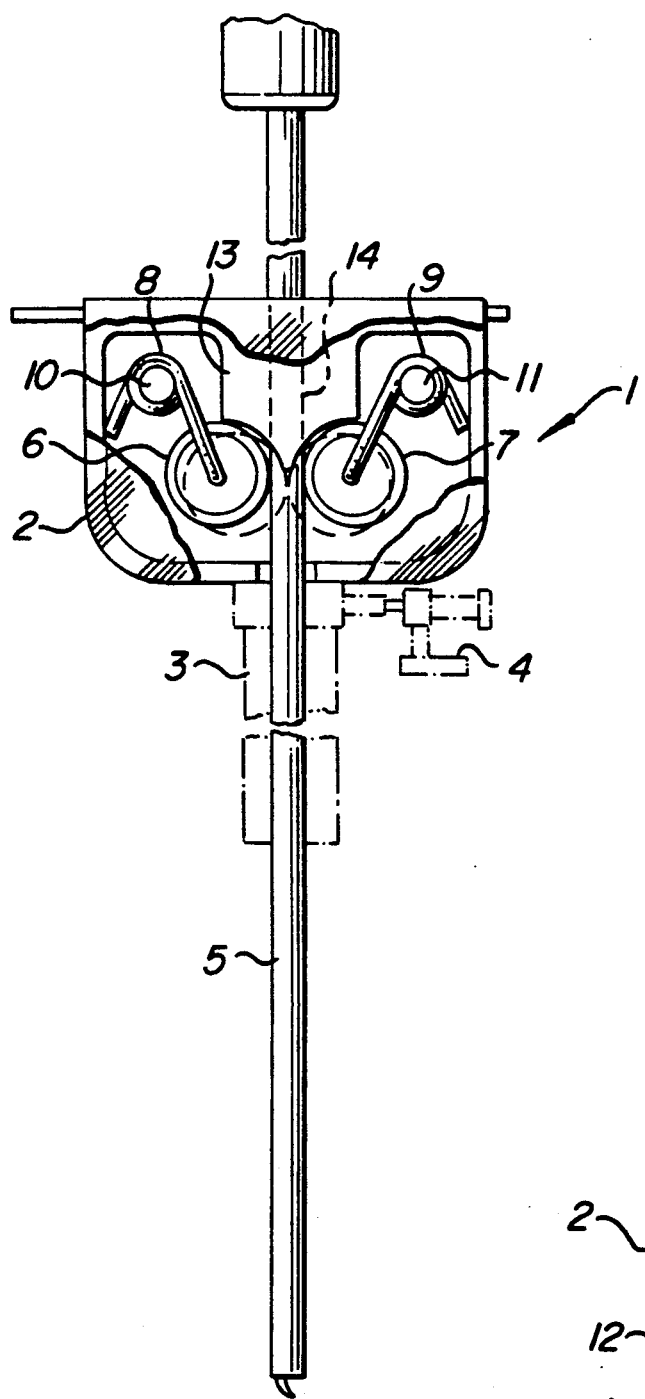
FIG. 1 is an elevational view of the cannula with a laparoscopic instrument passing through the cannula.

In FIG. 1 there is shown at 1 a cannula for use in laparoscopic surgery. The cannula comprises a housing 2 and an elongated hollow tube 3 fixed to the bottom wall of the housing. Only the upper end portion of the hollow tube 3 is shown and a valve 4 is attached to the tube to admit gas through the tube into the abdominal cavity.

In use, a trocar 5 is passed through the housing and through the hollow tube 3 to cut an incision in the abdominal wall. The trocar is then removed and the valve 4 is opened for insufflation of the abdomen. The cannula remains in place and serves to admit laparoscopic surgical instruments to enter the abdomen while maintaining a seal to prevent the escape of the pressurized gas within the abdomen.

Figure 2:
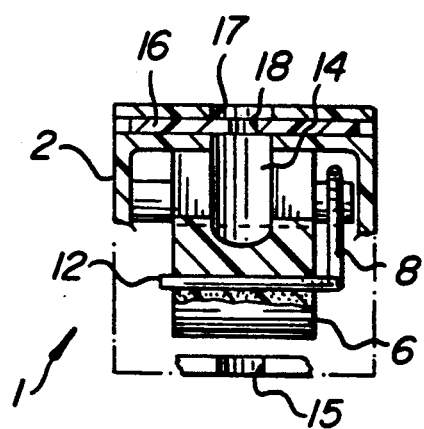
FIG. 2 is a cross sectional view along the lines A—A of FIG. 3 with the roller shown in partial sectional view.

As shown in FIG. 1 there are provided a pair of rollers 6 and 7 mounted on spring members 8 and 9 respectively which urge the rollers 6 and 7 towards the center of the housing. The spring members 8 and are mounted on fixed pins 10 and 11 respectively and, as shown, one arm of each spring engages a side wall of the housing and the other arm of the spring engages a roller to urge the rollers into contact with each other. Referring to FIG. 2 it can be seen that the end portion of an arm of spring 8 is bent to form a shaft 12 which extends through roller 6 to provide an axis for rotation of the roller. Roller 7 is similarly mounted on an arm of spring 9.

Figure 4:
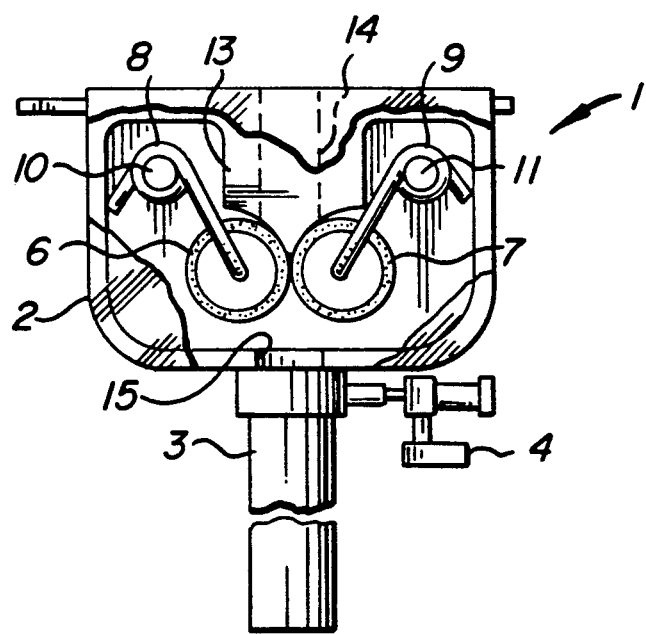
FIG. 4 is a sectional view along the lines B—B of FIG. 3.
Figure 5:
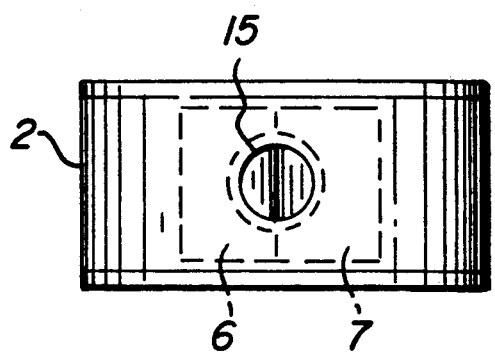
FIG. 5 is a bottom plan view of the cannula.

The housing 1 has a centrally disposed downwardly extending block 13 having a central passageway 14 extending therethrough as shown in FIG. 4. The lower faces of the block 13 are curved to receive the rollers 6 and 7 as shown in FIG. 4. When a trocar or other surgical instrument is not disposed within the cannula, the rollers 6 and 7 are spring-pressed into contact with each other to close off the passageway 14 and thus prevent escape of pressurized gas from the abdominal cavity. In FIG. 5 there is shown a bottom plan view of the housing 2 and showing in dotted lines the rollers 6 and 7 in face to face engagement to prevent pressurized air which passes into the housing 2 through opening 15 in the bottom wall of the housing from escaping to atmosphere.

Figure 3:
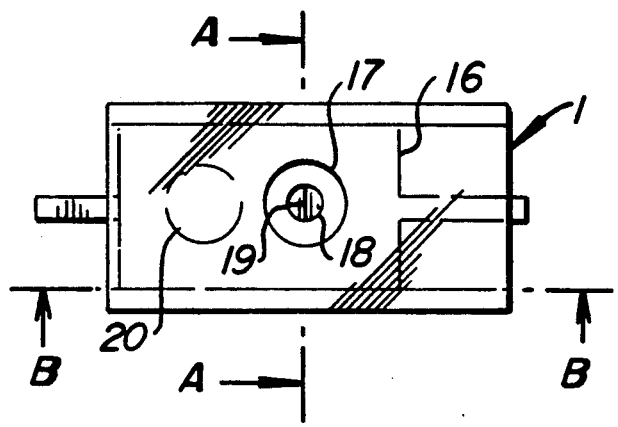
FIG. 3 is a top plan view of the cannula.

There is provided in the top wall of the housing 2 a slidable plate as shown at 16 in FIG. 3. This slidable plate fits within a slot formed in the top of the housing member as shown in FIG. 2. The plate has apertures therein of two different sizes and the plate can be positioned so that either the large or small opening in the plate is disposed between the opening 17 in the top of the housing member 1. As shown in FIG. 3, the smaller opening 18 is disposed directly beneath aperture 17 which is, of course, aligned with passageway 14 within the housing 1. The opening 18 is provided with an elastic diaphragm completely covering the opening and having a slit therein as shown at 19 in FIG. 3. When a trocar or surgical instrument having a small diameter is passed through the opening 18, the elastic diaphragm opens along slit 19 to permit the passage therethrough of the trocar or surgical instrument. The elastic diaphragm forms a tight seal surrounding the instrument to prevent outflow of the pressurized gas within the abdomen.

When larger sized trocars or surgical instruments are required, the plate 16 is slid to a position where the larger aperture 20 is in alignment with the aperture 17. Aperture 20 is also provided with an elastic diaphragm which is slitted so as to permit the larger diameter trocar or surgical instrument to pass through the passageway in the cannula without loss of pressurized gas.

Figure 6:
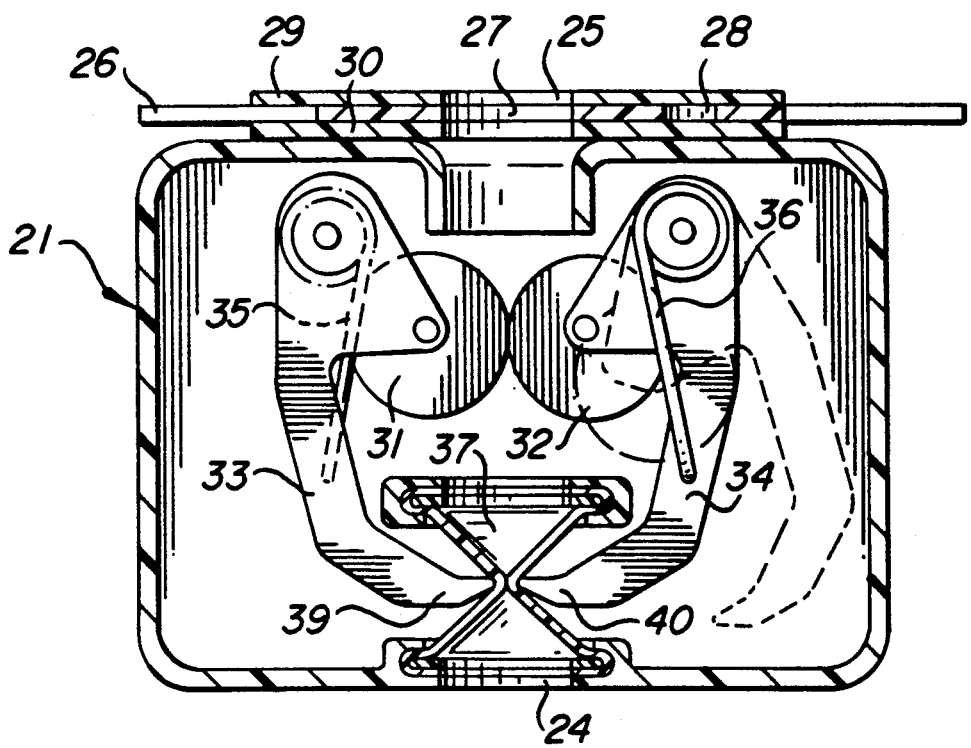
FIG. 6 is a cross sectional elevational view of another embodiment of the cannula.
Figure 7:
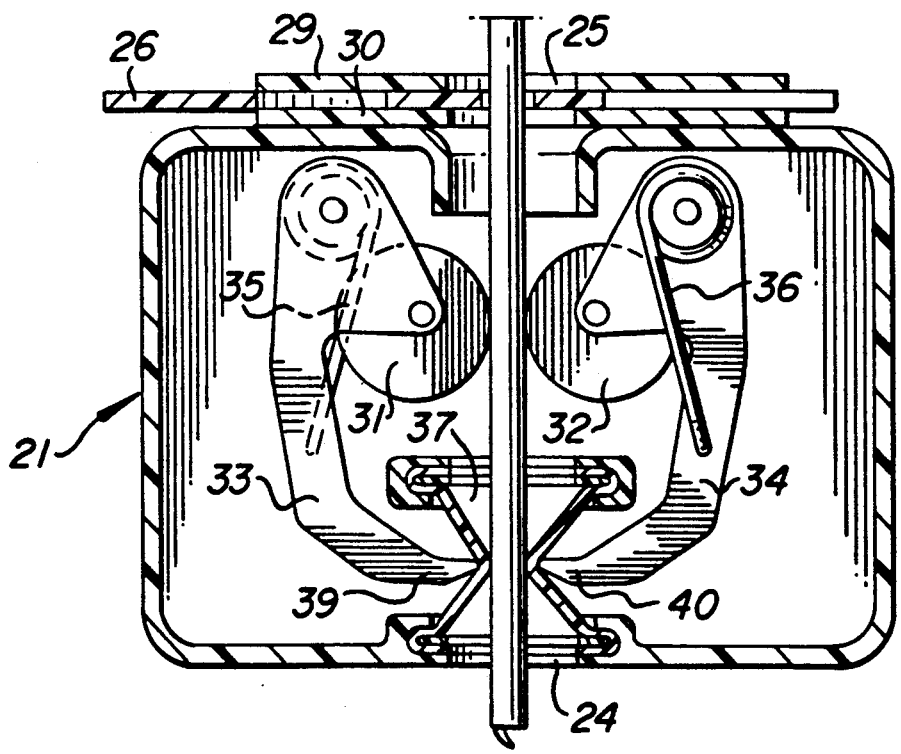
FIG. 7 is a sectional view showing the passage of a laparoscopic instrument through the cannula.

In FIGS. 6 and 7, there is a disclosed a further embodiment of the present invention. In this embodiment, a housing 21 is provided with aligned openings 24 and 25 in the bottom and top walls respectively. There is further provided a slidable plate 26 having a large aperture 27 and a small aperture 28 having slitted flexible diaphragms similar to those described in the FIG. 1 to 5 embodiment. As shown in FIGS. 6 and 7, the plate 26 is slidable within a slot formed between members 29 and 30.

Within the housing there are disposed a pair of rollers 31 and 32 which rollers are rotatably mounted on pivot arms 33 and 34 respectively and springs 35 and 36 respectively urge the rollers to an abutting position as shown in FIG. 6.

Disposed beneath the rollers 31 and 32 is an elastic valve member comprising an elastic sleeve 37 which is retained in position above the aperture 24 on the bottom wall of housing 21. The elastic sleeve 37 is supported at the upper end by a fixed frame 38 which has a central aperture therein in alignment with the aperture.

The pivotal arms 35 and 36 have extensions thereon as shown at 39 and 40 respectively and it can be seen that when the rollers 31 and 32 are in abutting relationship, the arms 39 and 40 are forced into the flexible sleeve 37 so as to close off the passageway between openings 24 and 25 in the bottom wall and top wall respectively of the housing 21. Referring to FIG. 7 it can be seen that a trocar for surgical instrument 40 has been passed through the passageway 25 between the rollers 31 and 32 which forces the arms 39 and 40 outwardly so as to permit the trocar to pass through the flexible sleeve valve 37 and through the passageway 24.

The rollers 31 and 32 in this embodiment of the invention do not perform the function of providing a seal as in the embodiment of FIGS. 1 to 5, the rollers 31 and 32 perform the function of opening and closing the flexible sleeve valve 37.

Obviously many modifications and variations of the present invention are possible in light of the foregoing teachings.

What is claimed as new and is desired to be secured by Letters Patents is:

1. A cannula for use with laparoscopic instruments comprising a housing having a bottom wall, top wall and sidewalls, said housing having a passageway extending through the top and bottom walls, a hollow tube extending from the bottom wall of the housing, a pair of rollers disposed within the housing, means mounting said rollers to urge the rollers together so as to close the passageway within said housing, said means permitting said rollers to separate and open the passageway when a laparoscopic instrument is passed into the passageway.

2. A cannula according to claim 1 and further including means for sealing the passageway when a laparoscopic instrument is passed into the passageway.

3. A cannula according to claim 2 wherein said means for sealing the passageway comprises a slidable plate having a plurality of apertures therein to receive laparoscopic instruments of varying diameters.

4. A cannula according to claim 3 and further including slitted seals disposed in said apertures.

5. A cannula according to claim 1 and further including a flexible valve disposed in the passageway beneath the rollers and pivotal arms extending downwardly from the rollers to engage said flexible valve so that when the rollers engage each other the flexible valve is forced to a closed position by said pivotal arms and when a laparoscopic instrument is forced between the rollers the flexible valve is opened to pass the laparoscopic instrument therethrough.

6. A cannula for use with laparoscopic instruments comprising, in combination, a hollow housing having top, bottom and side walls, aligned apertures in the top and bottom walls to form a passageway between the apertures, a pair of spring mounted rollers disposed within said housing, said rollers being urged together to close the passageway between said aligned apertures and means for sealing closed at least one of said aligned apertures.

7. A cannula according to claim 6 wherein said sealing means including a slidable plate having openings therein of different diameters and having slitted flexible sealing discs disposed in said apertures.

8. A cannula for use with laparoscopic instruments comprising a housing having a bottom wall, top wall and sidewalls, said housing having openings in the top and bottom walls of said housing, a hollow tube extending from the bottom wall of the housing, the openings in the top and bottom walls and the hollow tube being sufficiently large to receive laparoscopic instruments of a large diameter and further including sealing means mounted on the housing and extending over one of the openings in the housing for receiving laparoscopic instruments of varying diameters and for maintaining a seal around the laparoscopic instruments when the laparoscopic instruments are passed through the cannula, said sealing means including a slidable plate having openings therein of different diameters.

* * * * *